(12) United States Patent
Cai et al.

(10) Patent No.: US 7,102,002 B2
(45) Date of Patent: Sep. 5, 2006

(54) PYRROLOTRIAZINE KINASE INHIBITORS

(75) Inventors: Zhen-wei Cai, Belle Mead, NJ (US); Louis J. Lombardo, Belle Mead, NJ (US); Rajeev S. Bhide, Princeton Junction, NJ (US); Ligang Qian, Hopewell, NJ (US); Donna D. Wei, Belle Mead, NJ (US); Stephanie Barbosa, Lambertville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/152,650

(22) Filed: Jun. 14, 2005

(65) Prior Publication Data

US 2006/0009454 A1  Jan. 12, 2006

Related U.S. Application Data

(60) Provisional application No. 60/580,194, filed on Jun. 16, 2004.

(51) Int. Cl.
C07D 487/04 (2006.01)
A61K 31/53 (2006.01)
A61P 35/00 (2006.01)

(52) U.S. Cl. ...................................... 544/183; 514/243
(58) Field of Classification Search ................ 544/183; 514/243
See application file for complete search history.

(56) References Cited

U.S. PATENT DOCUMENTS

| | | | |
|---|---|---|---|
| 6,670,357 B1 | 12/2003 | Leftheris et al. | |
| 6,787,545 B1 | 9/2004 | Ohtani et al. | |
| 6,867,300 B1 | 3/2005 | Godfrey, Jr. et al. | |
| 6,869,952 B1 | 3/2005 | Bhide et al. | |
| 6,908,916 B1 | 6/2005 | Mastalerz et al. | |
| 6,916,815 B1 | 7/2005 | Vite et al. | |
| 2003/0232831 A1 | 12/2003 | Dyckman et al. | |
| 2003/0232832 A1 | 12/2003 | Lombardo et al. | |
| 2004/0063707 A1 | 4/2004 | Bhide et al. | |
| 2004/0063708 A1 | 4/2004 | Bhide et al. | |
| 2004/0077858 A1 | 4/2004 | Bhide et al. | |
| 2004/0229877 A1 | 11/2004 | Leftheris et al. | |

FOREIGN PATENT DOCUMENTS

| | | |
|---|---|---|
| EP | 0 713 876 | 5/1996 |
| WO | WO 98/08847 | 3/1998 |
| WO | WO 00/71129 | 11/2000 |
| WO | WO 02/40486 | 5/2002 |
| WO | WO 03/090912 | 11/2003 |
| WO | WO 2004/009784 | 1/2004 |

OTHER PUBLICATIONS

Cecil Textbook of Medicine, edited by Bennet, J.C., and Plum F., 20th edition, vol. 1, 1004-1010, 1996.*
Wolft Manfred E. "Burger's Medicinal Chemistry, 5ed, Part 1", John Wiley & Sons, 1995, pp. 975-977.*
Banker, G.S. et al, "Modern Pharmceutices, 3ed.", Marcel Dekker, New York 1996, pp. 451 and 596.*
Mass, R. D., Int. J. Radiation Oncology Bio. Phys. vol. 58(3): 932-940, 2004.*
West, Anthony R., Solid State Chemistry and its Applications, Wiley, New York, 1988, pp. 358 & 365.*
Vippagunta et al., Advanced Drug Delivery Reviews 48: 3-26, 2001.*
And Fabbro et al. Pharmacology & therapeutics 93, 79-98, 2002.*
U.S. Appl. No. 60/620,784, filed Oct. 21, 2004, Gavai et al.
U.S. Appl. No. 11/008,719, filed Dec. 9, 2004, Swaminathan et al.
U.S. Appl. No. 11/019,899, filed Dec. 22, 2004, Gavai et al.
U.S. Appl. No. 11/019,901, filed Dec. 22, 2004, Fink et al.
U.S. Appl. No. 11/157,460, filed Jun. 21, 2005, Gavai et al.
Ewald, H. et al., "Reaktionen von 1,2,4-Triazinen mit Acetylendicarbonsäure-dimethylester", Liebigs Ann. Chem., pp. 1718-1724 (1977).
Hunt, J.T et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-f]-1,2,4-triazine Derivatives", J. Heterocyclic Chem., vol. 16, pp. 833-834 (1979).
Neunhoeffer, H. et al., "Cycloadditionen mit Methoxy- und Dialkylamino-1,2,4-triazinen", Liebigs Ann. Chem., pp. 1413-1420 (1977).
Patil, S.A. et al., "Synthesis of Pyrrolo[2,1-f][1,2,4]triazine Congeners of Nucleic Acid Purines via the N-Amination of 2-Substituted Pyrroles", J. Heterocyclic Chem., vol. 31, pp. 781-786 (1994).
Quintela, J.M. et al., "A Ready One-pot Preparation for Pyrrolo[2,1-f][1,2,4]triazine and Pyrazolo[5,1-c]pyrimido[4,5-e]-[1,2,4]triazine Derivatives", Tetrahedron, vol. 52, No. 8, pp. 3037-3048 (1996).

* cited by examiner

Primary Examiner—Venkataraman Balasubramanian
(74) Attorney, Agent, or Firm—Elliott Korsen

(57) ABSTRACT

The present invention provides compounds of formula I,

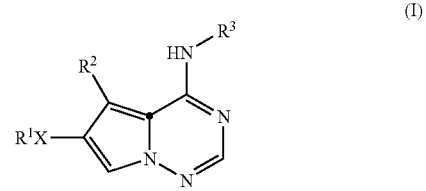

(I)

and pharmaceutically acceptable salts thereof.

The formula I compounds inhibit the tyrosine kinase activity of growth factor receptors such as VEGFR-2 and FGFR-1, thereby making them useful as anti-cancer agents. The formula I compounds are also useful for the treatment of other diseases associated with signal transduction pathways operating through growth factor receptors.

6 Claims, No Drawings

PYRROLOTRIAZINE KINASE INHIBITORS

This application claims priority to provisional application No. 60/580,194, filed Jun. 16, 2004, which is herein incorporated by reference in its entirety.

FIELD OF THE INVENTION

This invention relates to compounds that inhibit the tyrosine kinase activity of growth factor receptors such as VEGFR-2, and FGFR-1, thereby making them useful as anti-cancer agents. The compounds are also useful in the treatment of diseases, other than cancer, which are associated with signal transduction pathways operating through growth factor and anti-angiogenesis receptors such as VEGFR-2.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, rheumatoid arthritis, atheroma, Kaposi's sarcoma and haemangioma, asthma, cancer and metastatic disease (Fan et al, 1995, Trend Pharmacol. Sci. 16: 57–66; Folkman, 1995, Nature Medicine 1: 27–31). Alteration of vascular permeability is thought to play a role in both normal and pathophysiological processes (Cullinan-Bove et al, 1993, Endocrinology 133: 829–837; Senger et al, 1993 Cancer and Metastasis Reviews, 12: 303–324).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised of the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. It is noted that aFGF and bFGF bind to and activate the receptor tyrosine kinase termed FGFR-1. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36: 139–155) and vascular permeability (Connolly et al, 1989, J. Biol. Chem. 264: 20017–20024).

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. It is now widely accepted that the ability of tumors to expand and metastasize is dependent upon the formation of this vascular network.

Binding of VEGF or bFGF to their corresponding receptor results in dimerization, autophosphorylation on tyrosine residues and enzymatic activation. These phosphotyrosine residues serve as "docking" sites for specific downstream signaling molecules and enzymatic activation results in EC activation. Disruption of these pathways should inhibit endothelial cell activation. Disruption of the FGFR-1 pathway should also affect tumor cell proliferation since this kinase is activated in many tumor types in addition to proliferating endothelial cells. Finally, recent evidence also suggests that disruption of VEGF signaling inhibits endothelial cell migration, a critical process in vascular network formation.

The over-expression and activation of VEGFR-2 and FGFR-1 in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

DETAILED DESCRIPTION OF THE INVENTION

In accordance with the present invention, compounds of formula I,

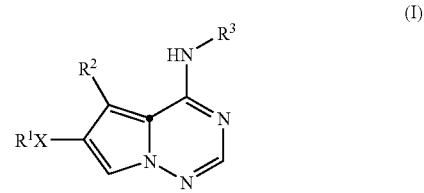

their enantiomers, diastereomers, and pharmaceutically acceptable salts, prodrugs and solvates thereof, inhibit the tyrosine kinase activity of growth factor receptors such as VEGFR-2.

In formula I and throughout the specification, the above symbols are defined as follows:

X is —O—,

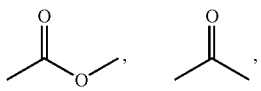

—OCONH—, —S—, —SO— or —SO$_2$—, or X is absent;

R$^1$ is hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl or substituted heterocycloalkyl R$^2$ is hydrogen, alkyl or substituted alkyl;

R$^3$ is

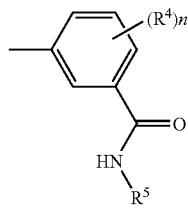

wherein
each R$^4$ is independently selected from hydrogen, halogen or alkyl;
n is 0, 1 or 2; and
R$^5$ is hydrogen, alkyl, substituted alkyl, cycloalkyl, substituted cycloalkyl, heterocyclyl or substituted heterocyclyl.

In one embodiment of the invention, there is disclosed a compound of Formula 1 wherein x is —O—,

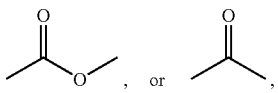

or X is absent;

R$^1$ is alkyl, substituted alkyl, aryl, substituted aryl, heterocyclo, substituted heterocyclo, aralkyl, substituted aralkyl, heterocycloalkyl or substituted heterocycloalkyl R$^2$ is alkyl;

R$^3$ is

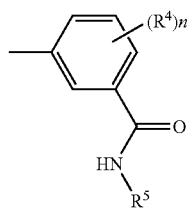

wherein
each R$^4$ is independently selected from hydrogen or halogen;
n is 1 or 2; and R$^5$ is cycloalkyl.

In another embodiment of the invention, there is disclosed a compound of Formula 1 wherein X is absent;

R$^1$ is heterocyclo, substituted heterocyclo, heterocycloalkyl or substituted heterocycloalkyl;

R$^2$ is alkyl;

R$^3$ is

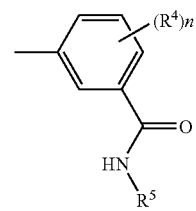

wherein
each R$^4$ is independently selected from hydrogen or fluorine;
n is 1 or 2; and
R$^5$ is cyclopropyl.

In another embodiment of the invention, there is disclosed a compound of Formula 1 wherein X is absent;

R$^1$ is oxadizole or substituted oxadiazole;

R$^2$ is isopropyl;

R$^3$ is

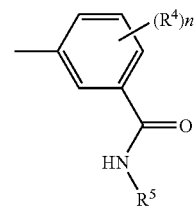

wherein
each R$^4$ is independently selected from hydrogen or fluorine;
n is 1 or 2 and
R$^5$ is cyclopropyl.

Compounds of the invention include the following:

methyl 4-(5-(cyclopropylcarbamoyl)-2-fluorophenylamino)-5-isopropylpyrrolo[1,2-f][1,2,4]triazine-6-carboxylate, methyl 4-(5-(cyclopropylcarbamoyl)-2,4-difluorophenylamino)-5-isopropylpyrrolo[1,2-f][1,2,4]triazine-6-carboxylate, N-cyclopropyl-2,4-difluoro-5-(5-isopropyl-6-(5-(isopropylamino)-1,3,4-oxadiazol-2-yl)pyrrolo[1,2-f][1,2,4]triazin-4-ylamino)benzamide, N-cyclopropyl-2,4-difluoro-5-(6-(5-(2-hydroxyethylamino)-1,3,4-oxadiazol-2-yl)-5-isopropylpyrrolo[1,2-f][1,2,4]triazin-4-ylamino)benzamide, N-cyclopropyl-2,4-difluoro-5-(5-isopropyl-6-(5-(propylamino)-1,3,4-oxadiazol-2-yl)pyrrolo[1,2-f][1,2,4]triazin-4-ylamino)benzamide, N-cyclopropyl-2,4-difluoro-5-(6-(5-(2-fluoroethylamino)-1,3,4-oxadiazol-2-yl)-5-isopropylpyrrolo[1,2-f][1,2,4]triazin-4-ylamino)benzamide, N-cyclopropyl-5-(6-(5-(2-(ethylamino)ethylamino)-1,3, 4-oxadiazol-2-yl)-5-isopropylpyrrolo[1,2-f][1,2,4]triazin-4-ylamino)-2,4-difluorobenzamide, 5-(6-(5-(2-amino-2-methylpropylamino)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-2,4-difluoro-5-(6-(5-((S)-2-hydroxypropylamino)-1,3,4-oxadiazol-2-yl)-5-isopropylpyrrolo[1,2-f][1,2,4]triazin-4-ylamino)benzamide, N-cyclopropyl-2,4-difluoro-5-(6-(5-((R)-2-hydroxypropylamino)-1,3,4-oxadiazol-2-yl)-5-isopropylpyrrolo[1,2-f][1,2,4]triazin-4-ylamino)benzamide, N-cyclopropyl-2,4-difluoro-5-(6-(5-((R)-3-hydroxypyrrolidin-1-yl)-1,3,4-oxadiazol-2-yl)-5-isopropylpyrrolo[1,2-f][1,2,4]triazin-4-ylamino)benzamide, 5-(6-(5-(3-amino-2,2-dimethylpropylamino)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-2,4-difluoro-5-(5-isopropyl-6-(5-(piperazin-1-yl)-1,3,4-oxadiazol-2-yl)pyrrolo[1,2-f][1,2,4]triazin-4-ylamino)benzamide, N-cyclopropyl-5-(6-(5-(3-(dimethylamino)propylamino)-1,3,4-oxadiazol-2-yl)-5-isopropylpyrrolo[1,2-f][1,2,4]triazin-4-ylamino)-2,4-difluorobenzamide, 5-(6-(5-(4-aminopiperidin-1-yl)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-2,4-difluoro-5-(5-isopropyl-6-(5-(3-(methylamino)propylamino)-1,3,4-oxadiazol-2-yl)pyrrolo[1,2-f][1,2,4]triazin-4-ylamino)benzamide, 5-(6-(5-(3-aminopropylamino)-1,3,4-oxadiazol-2-yl)-5-isopropylpyrrolo[1,2-f][1,2,4]triazin-4-ylamino)-N-cyclopropyl-2,4-difluorobenzamide, 5-(6-(5-(4-aminobutylamino)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-2,4-difluoro-5-(5-isopropyl-6-(5-((R)-pyrrolidin-3-yloxy)-1,3,4-oxadiazol-2-yl)pyrrolo[1,2-f][1,2,4]triazin-4-ylamino)benzamide, 5-(6-(5-((R)-2-aminopropoxy)-1,3,4-oxadiazol-2-yl)-5-isopropylpyrrolo[1,2-f][1,2,4]triazin-4-ylamino)-N-cyclopropyl-2,4-difluorobenzamide, 5-(6-(5-((S)-2-aminopropoxy)-1,3,4-oxadiazol-2-yl)-5-isopropylpyrrolo[1,2-f][1,2,4]triazin-4-ylamino)-N-cyclopropyl-2,4-difluorobenzamide, 5-(6-(5-(2-amino-2-methylpropoxy)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-2,4-difluoro-5-(5-isopropyl-6-(5-((S)-pyrrolidin-3-yloxy)-1,3,4-oxadiazol-2-yl)pyrrolo[1,2-f][1,2,4]triazin-4-ylamino)benzamide, N-cyclopropyl-2,4-difluoro-5-(5-isopropyl-6-(5-(piperidin-4-yloxy)-1,3,4-oxadiazol-2-yl)pyrrolo[1,2-f][1,2,4]triazin-4-ylamino)benzamide, N-cyclopropyl-2,4-difluoro-5-(5-isopropyl-6-(5-(piperidin-4-ylmethoxy)-1,3,4-oxadiazol-2-yl)pyrrolo[1,2-f][1,2,4]triazin-4-ylamino)benzamide, 5-(6-(5-(3-amino-3-methylbutoxy)-1,3,4-oxadiazol-2-yl)-5-isopropylpyrrolo[1,2-f][1,2,4]triazin-4-ylamino)-N-cyclopropyl-2,4-difluorobenzamide, 5-(6-(5-(3-aminopropoxy)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-2,4-difluoro-5-(5-isopropyl-6-(5-(morpholinomethyl)-1,3,4-oxadiazol-2-yl)pyrrolo[1,2-f][1,2,4]triazin-4-ylamino)benzamide, 5-(6-(5-(aminomethyl)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-2,4-difluoro-5-(5-isopropyl-6-(5-((methylamino)methyl)-1,3,4-oxadiazol-2-yl)pyrrolo[1,2-f][1,2,4]triazin-4-ylamino)benzamide, N-cyclopropyl-2,4-difluoro-5-(6-(5-(((R)-2-hydroxypropylamino)methyl)-1,3,4-oxadiazol-2-yl)-5-isopropylpyrrolo[1,2-f][1,2,4]triazin-4-ylamino)benzamide, N-cyclopropyl-2,4-difluoro-5-(6-(5-(((S)-2-hydroxypropylamino)methyl)-1,3,4-oxadiazol-2-yl)-5-isopropylpyrrolo[1,2-f][1,2,4]triazin-4-ylamino)benzamide, N-cyclopropyl-2,4-difluoro-5-(6-(5-(((R)-3-hydroxypyrrolidin-1-yl)methyl)-1,3,4-oxadiazol-2-yl)-5-isopropylpyrrolo[1,2-f][1,2,4]triazin-4-ylamino)benzamide, N-cyclopropyl-2,4-difluoro-5-(6-(5-(((S)-3-hydroxypyrrolidin-1-yl)methyl)-1,3,4-oxadiazol-2-yl)-5-isopropylpyrrolo[1,2-f][1,2,4]triazin-4-ylamino)benzamide, N-cyclopropyl-2,4-difluoro-5-(5-isopropyl-6-(5-(piperazin-1-ylmethyl)-1,3,4-oxadiazol-2-yl)pyrrolo[1,2-f][1,2,4]triazin-4-ylamino)benzamide, N-cyclopropyl-5-(6-(5-((dimethylamino)methyl)-1,3,4-oxadiazol-2-yl)-5-isopropylpyrrolo[1,2-f][1,2,4]triazin-4-ylamino)-2,4-difluorobenzamide, N-cyclopropyl-2,4-difluoro-5-(5-isopropyl-6-(5-((isopropylamino)methyl)-1,3,4-oxadiazol-2-yl)pyrrolo[1,2-f][1,2,4]triazin-4-ylamino)benzamide, N-cyclopropyl-5-(6-(5-((ethylamino)methyl)-1,3,4-oxadiazol-2-yl)-5-isopropylpyrrolo[1,2-f][1,2,4]triazin-4-ylamino)-2,4-difluorobenzamide, N-cyclopropyl-2,4-difluoro-5-(6-(5-((2-hydroxyethylamino)methyl)-1,3,4-oxadiazol-2-yl)-5-isopropylpyrrolo[1,2-f][1,2,4]triazin-4-ylamino)benzamide, N-cyclopropyl-2,4-difluoro-5-(5-isopropyl-6-(5-((2-methoxyethylamino)methyl)-1,3,4-oxadiazol-2-yl)pyrrolo[1,2-f][1,2,4]triazin-4-ylamino)benzamide, 5-(6-(5-(((S)-2-aminopropoxy)methyl)-1,3,4-oxadiazol-2-yl)-5-isopropylpyrrolo[1,2-f][1,2,4]triazin-4-ylamino)-N-cyclopropyl-2,4-difluorobenzamide, N-cyclopropyl-3-(6-(5-(3-(dimethylamino)propylamino)-1,3,4-oxadiazol-2-yl)-5-isopropylpyrrolo[1,2-f][1,2,4]triazin-4-ylamino)-4-fluorobenzamide, 3-(6-(5-(3-aminopropylamino)-1,3,4-oxadiazol-2-yl)-5-isopropylpyrrolo[1,2-f][1,2,4]triazin-4-ylamino)-N-cyclopropyl-4-fluorobenzamide, 3-(6-(5-((S)-3-aminopyrrolidin-1-yl)-1,3,4-oxadiazol-2-yl)-5-isopropylpyrrolo[1,2-f][1,2,4]triazin-4-ylamino)-N-cyclopropyl-4-fluorobenzamide, 3-(6-(5-((R)-3-aminopyrrolidin-1-yl)-1,3,4-oxadiazol-2-yl)-5-isopropylpyrrolo[1,2-f][1,2,4]triazin-4-ylamino)-N-cyclopropyl-4-fluorobenzamide, N-cyclopropyl-4-fluoro-3-(5-isopropyl-6-(5-(pyrrolidin-3-ylamino)-1,3,4-oxadiazol-2-yl)pyrrolo[1,2-f][1,2,4]triazin-4-ylamino)benzamide, and pharmaceutically acceptable salts and prodrugs thereof.

The invention also provides a pharmaceutical composition comprising a compound of formula I and a pharmaceutically acceptable carrier.

The invention also provides a pharmaceutical composition comprising a compound of formula I in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin, razoxane, tamoxifen, toremifene; raloxifene, droloxifene, iodoxifene, megestrol acetate, anastrozole, letrozole, borazole, exemestane, flutamide, nilutamide, bicalutamide, cyproterone acetate, gosereline acetate, leuprolide, finasteride; metalloproteinase inhibitors; inhibitors of urokinase plasminogen activator receptor function; growth factor antibodies; growth factor receptor antibodies such as Avastin® (bevacizumab) and Erbitux® (cetuximab); tyrosine kinase inhibitors; serine/threonine kinase inhibitors; methotrexate, 5-fluorouracil, purine, adenosine analogues, cytosine arabinoside, doxorubicin, daunomycin, epirubicin, idarubicin, mitomycin-C, dactinomycin, mithramycin, cisplatin, carboplatin, nitrogen mustard, melphalan, chlorambucil, busulphan, cyclophosphamide, ifosfamide, nitrosoureas, thiotepa, vincristine, Taxol® (paclitaxel), Taxotere® (docetaxel), epothilone analogs, discodermolide analogs, eleutherobin analogs, etoposide, teniposide, amsacrine, topotecan, flavopyridols; biological response modifiers and proteasome inhibitors such as Velcade® (bortezomib).

The invention also provides a method of inhibiting protein kinase activity of growth factor receptors which comprises administering to a mammalian species in need thereof, a therapeutically effective protein kinase inhibiting amount of a compound of formula I.

Additionally, there is disclosed a method of inhibiting tyrosine kinase activity of at least one growth factor receptor such as which comprises administering to a mammalian species in need thereof, a therapeutically effective amount of a compound of formula I. In a preferred embodiment said growth factor receptor is selected from the group consisting of VEGFR-2 and FGFR-1.

Finally, there is disclosed a method for treating a proliferative disease, comprising administering to a mammalian species in need thereof, a therapeutically effective amount of a compound of formula I. In a preferred embodiment the proliferative disease is cancer.

Definitions

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic", "heterocyclyl" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, benzimidazole, dihydrobenzofuryl, indolyl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclos, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I may also have prodrug forms. Any compound that will be converted in vivo to provide the bioactive agent (i.e., the compound for formula I) is a prodrug within the scope and spirit of the invention.

Various forms of prodrugs are well known in the art. A comprehensive description of prodrugs and prodrug derivatives are described in:

The Practice of Medicinal Chemistry, Camille G. Wermuth et al., Ch 31, (Academic Press, 1996);

Design of Prodrugs, edited by H. Bundgaard, (Elsevier, 1985);

A Textbook of Drug Design and Development, P. Krogsgaard-Larson and H. Bundgaard, eds. Ch 5, pgs 113–191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

It should further be understood that solvates (e.g., hydrates) of the compounds of formula I are also with the scope of the present invention. Methods of solvation are generally known in the art.

Use and Utility

The present invention is based on the discovery that certain pyrrolotriazines are inhibitors of protein kinases. More specifically, they inhibit the effects of VEGF, a property of value in the treatment of disease states associated with angiogenesis and/or increased vascular permeability such as cancer. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung. In another embodiment, the compounds of the present invention are also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetes-induced renal disease), atheroma, arterial restenosis, autoimmune diseases, acute inflammation and ocular diseases with retinal vessel proliferation, diabetic retinopathy, retinopathy of prematurity and macular degeneration. The invention also relates to prevention of blastocyte implantation in a mammal, treatment of atherosclerosis, eczema, scleroderma, hemangioma. Compounds of the present invention posses good activity against VEGF receptor tyrosine kinase while possessing some activity against other tyrosine kinases.

Thus according to a further aspect of the invention, there is provided the use of a compound of formula I, or a pharmaceutically acceptable salt thereof in the manufacture of a medicament for use in the production of an antiangiogenic and/or vascular permeability reducing effect in a mammalian animal such as a human being.

According to a further feature of the invention there is provided a method for producing an antiangiogenic and/or vascular permeability reducing effect in a mammalian animal, such as a human being, in need of such treatment which comprises administering to said animal an effective amount of a compound of formula I or a pharmaceutically acceptable salt thereof as defined herein before.

The antiproliferative, antiangiogenic and/or vascular permeability reducing treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates like methotrexate, fluoropyrimidines like 5-fluorouracil, purine and adenosine analogues, cytosine arabinoside); intercalating antitumour antibiotics (for example, anthracyclines like doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinblastine and vinflunine, and taxoids like Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins like etoposide and teniposide, amsacrine, topotecan); cell cycle inhibitors (for example, flavopyridols); biological response modifiers and proteasome inhibitors such as Velcade® (bortezomib).

As stated above, the formula I compounds of the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkitt's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as VEGFR-2.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.™. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 800 mg/kg/day, preferably less than 500 mg/kg/day, in a single dose or in 2 to 4 divided doses.

Biological Assays

VEGFR-2 and FGFR-1 Kinase Assays

| Reagents | Final Concentration | |
|---|---|---|
| Stock Solution | VEGFR-2 | FGFR-1 |
| Tris pH 7.0 | 20 mM | 20 mM |
| BSA 10 mg/ml | 25 µg/ml | 25 µg/ml |
| $MnCl_2$ (1 M) | 1.5 mM | 0.5 mM |
| $MgCl_2$ (1 M) | — | 0.5 mM |
| DTT(1 M) | 0.5 mM | 0.5 mM |
| Enzyme Stock in 10% glycerol (1 mg/ml) | 5 ng/rxn | 20 ng/rxn |
| Polyglu/tyr (10 mg/ml) | 75 µg/ml | 30 µg/ml |
| ATP (1 mM) | 2.5 µM | 1.0 µM |
| γ-ATP (10 µCi/µl) | 0.5 µCi/ml | 0.5 µCi |

Incubation mixtures employed for VEGFR-2 or FGFR-1 assay contain the synthetic substrate polyGlu:Tyr, (4:1), ATP, ATP-γ-$^{33}$P and buffer containing $Mn^{++}$ and/or $Mg^{++}$, DTT, BSA, and Tris buffer. The reaction is initiated by addition of enzyme and after 60 minutes is terminated by the addition of TCA to 30%. Inhibitors are brought to 10 mM in 100% DMSO. Assays are prepared in a 96 well format. Compounds are diluted 1:500 in 100% DMSO and then 1:10 in water for a final DMSO concentration of 10%. 10 µL are added to rows B–H in a 96 well format of 10% DMSO. 20 µl of compound is added to row A at a concentration 5 fold higher than running conditions. Ten µL are transferred to each row with 10 pippetting phases for mixing, and at row F 10 µL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard FilterMate harvester. Activity is determined by quantitating the incorporated radioactivity using a Packard TopCount Microplate Scintillation Counter following the addition of Microscint-20 cocktail into each dried well of the UniFilter microplates.

The instant compounds inhibit VEGFR-2 and FGFR-1 kinases with $IC_{50}$ values between 0.01 to 10 µM. Preferred compounds have $IC_{50}$ values less than 0.3 µM.

These compounds are selective against VEGFR-2 and FGFR-1 kinase enzymes. They have minimum activity against CDK-2 kinase and LCK and Src kinases. Activity against these kinases is >1 μM.

In addition, other compounds of formula I may be prepared using procedures generally known to those skilled in the art. In particular, the following examples provide additional methods for preparing compounds of this invention.

The invention will now be further described by the following working examples. These examples are illustrative rather than limiting, and it is to be understood that there may be other embodiments that fall within the spirit and scope of the invention as defined by the claims appended hereto.

All temperatures are in degrees Celsius (° C.) unless otherwise indicated. Reverse Phase (RP) HPLC purifications were done on C18 reverse phase (RP) columns using water methanol mixtures and 0.1% TFA as buffer solution. All the synthesized compounds were characterized by at least proton NMR and LC/MS. During work up of reactions, the organic extract was dried over magnesium sulfate (MgSO$_4$), unless mentioned otherwise. Following abbreviations are used for the commonly used reagents. NMM; N-methylmorpholine, DIBALH; diisobutylaluminum hydride, BOP reagent; benzotriazol-1-yloxy-tris(trimethylamino)phosphonium hexafluorophosphate, DCE; dichloroethane, K$_2$CO$_3$; potassium carbonate, KOH; potassium hydroxide, DCC; dicyclohexyl carbodiimide, EDCI; 1-(dimethylaminopropyl)-3-ethylcabodiimide hydrochloride, RT; room temperature, HOBt; hydroxybenzotriazole, DCM; dichloroethane, CbzCl; chlorobenzoyl chloride, NaHCO$_3$; sodium bicarbonate, HCl; hydrochloric acid, TFA; trifluoroacetic acid, NH$_4$Cl; ammonium chloride, DIPEA; diisopropylamine, Et$_3$N; triethylamine, RT; room temperature.

Methods of Preparation

Certain compounds of formula I may be prepared according to the following schemes and the knowledge of one skilled in the art.

Scheme 1

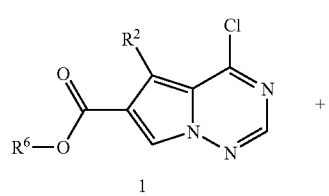

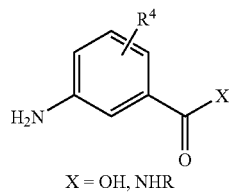

-continued

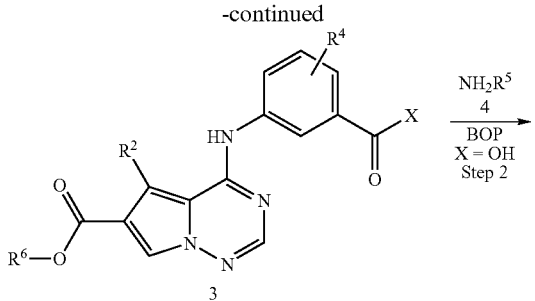

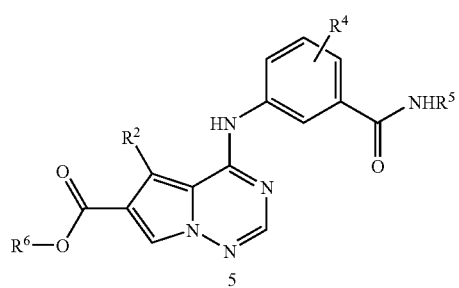

(R$^6$ is alkyl or substituted alkyl)

Step 1: The first step is accomplished by refluxing of chloroimidate 1 and substituted aniline 2 in acetonitrile to afford product 3. This procedure is disclosed in US 2004/63708A1.

Step 2: The product 5 is obtained by treatment of carboxylic acid substituted product 3 with an amine 4 in the presence of coupling agent such as benzotriazole-1-yl-oxy-tris(dimethylamino)-phosphoniumhexafluoro-phosphate (BOP) with an organic base such as triethylamine, in an organic solvent such as N,N-dimethylformamide (DMF).

Scheme 2

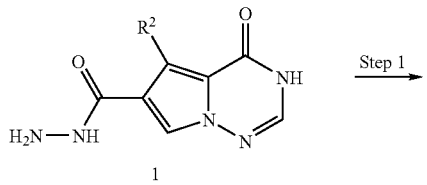

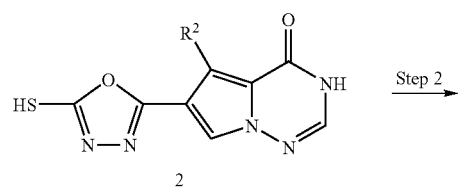

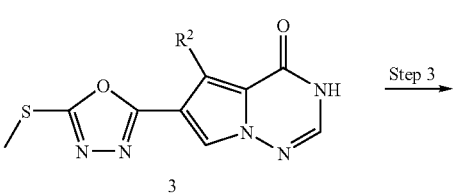

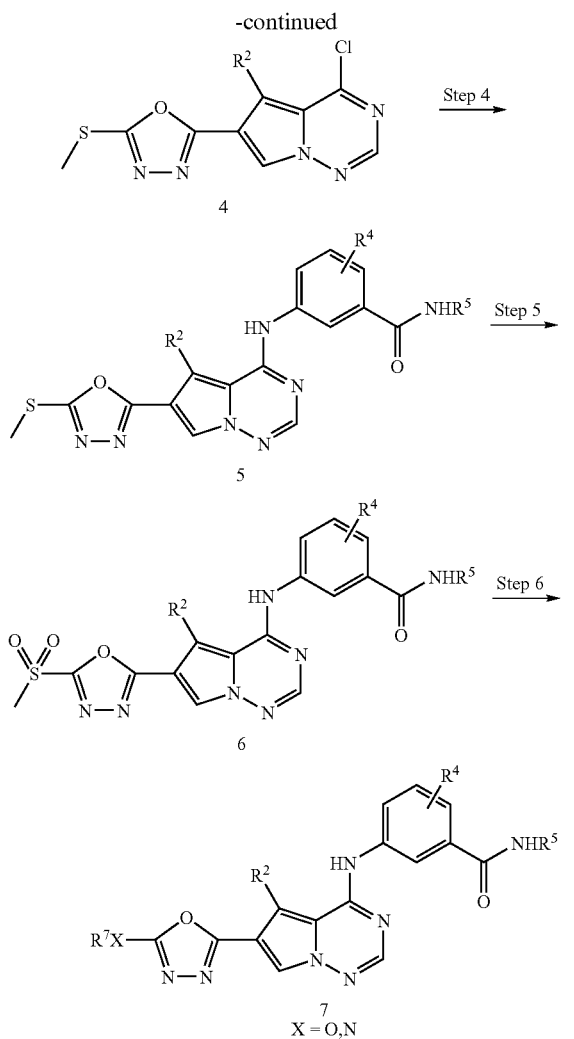

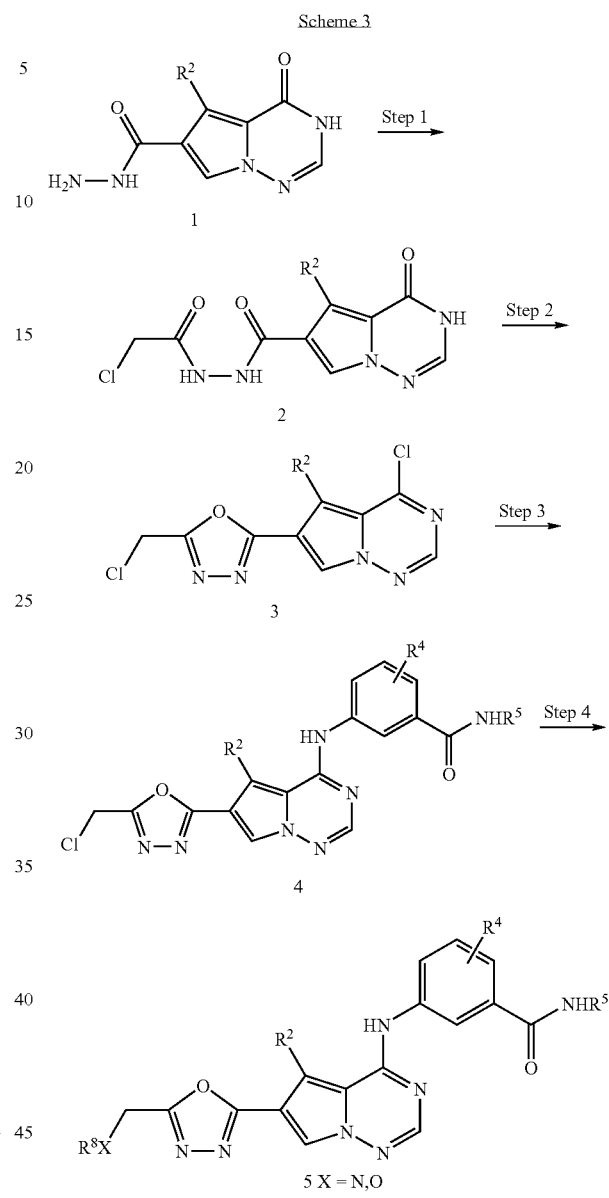

Step 1: The carbohydrazide 1 is treated with 1,1'-thiocarbonyldiimidazole in an organic solvent such as N,N-dimethylformamide, and the mixture is cyclized at elevated temperature to give oxadiazole mercapto intermediate 2.

Step 2: Alkylation of mercapto 2 was with alkyl halide such as methyl iodide to form sulfide 3.

Step 3: The intermediate 3 is reacted with dehydrating agent such as phosphorous oxychloride at 110° C. to afford 4.

Step 4: The chloroimidate 4 is treated with appropriate anilines in solvent such as acetonitrile at refluxing temperature to provide 5.

Step 5: Treatment of compound 5 with an oxidant, such as m-chloroperbenzoic acid (m-CPBA), in an organic solvent, such as dichloromethane (DCM), affords sulfone 6.

Step 6: Treatment of 6 with an amine in an organic solvent such as 1,4-dioxane at elevated temperature to give substituted oxadiazole product 7 (X=N).

Treatment of 6 with alkoxide metal salt such as sodium salt in an organic solvent such as tetrahydrofuran (THF) at lower temperature to afford alkyloxy substituted oxadiazole product 7 (X=O).

Step 1: The carbohydrazide 1 is treated with chloroacetyl chloride in organic co-solvent such as N,N-dimethylformamide (DMF), tetrahydrofuran (THF), and pyridine at 0° C. to afford the intermediate 2.

Step 2: The intermediate 2 is reacted with dehydrating agent such as phosphorous oxychloride at elevated temperature to form intermediate 3.

Step 3: The chloroimidate 3 is treated with appropriate anilines in solvent such as acetonitrile at refluxing to provide 4 as described in Scheme 1.

Step 4: Treatment of compound 4 with an amine in an organic solvent, such as tetrahydrofuran (THF) at 25–50° C., affords product 5 where X=N.

Treatment of alkoxide such as sodium salt in an organic solvent, such as tetrahydrofuran (THF) at 0° C. affords product 5 where X=O.

Scheme 4

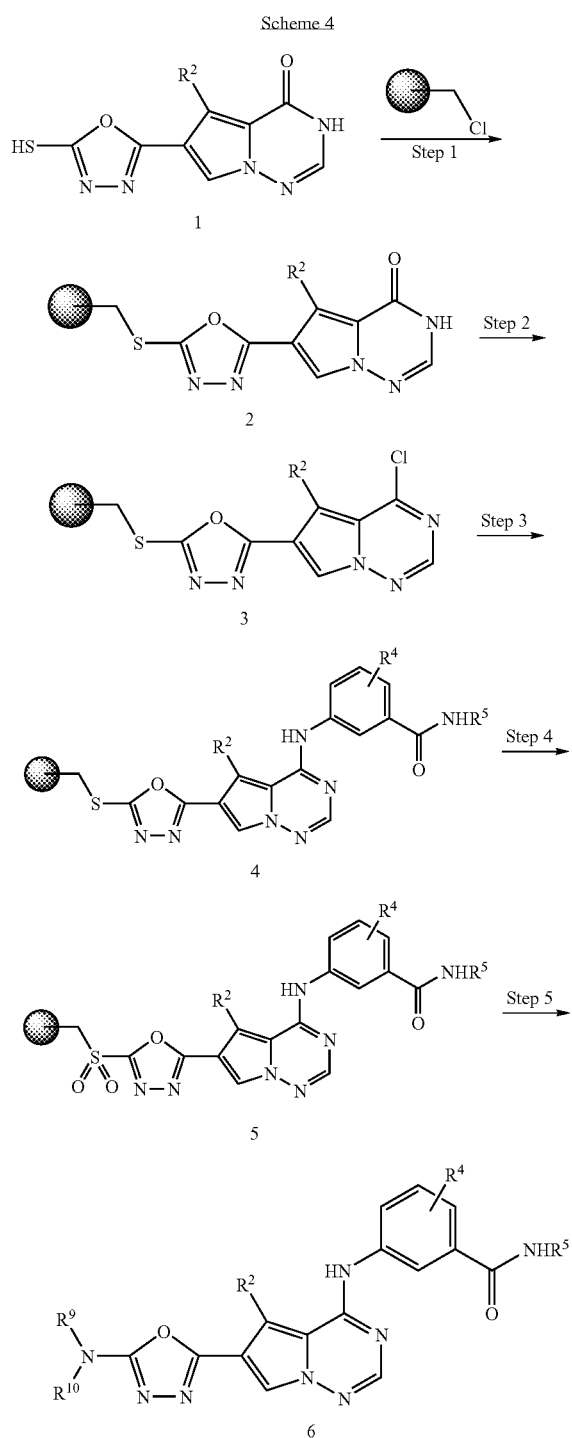

Step 3: The chloroimidate 3 is treated with appropriate anilines in co-solvents such as acetonitrile and 1,2-dichloroethane (DCE) at 80° C. to provide 4.

Step 4: Treatment of resin 4 with an oxidant, such as m-chloroperbenzoic acid (mCPBA), in an organic solvent, such as dichloromethane (DCM), affords resin bound sulfone 5.

Step 5: Product 6 is cleaved from resin upon treatment of resin 5 with an amine in an organic solvent such as 1,4-dioxane at elevated temperature.

EXAMPLE 1

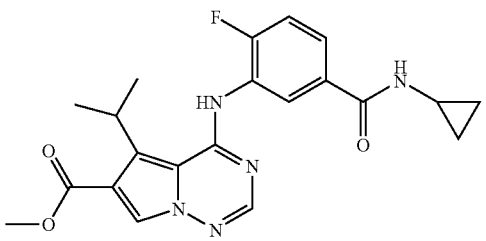

A mixture of methyl 4-chloro-5-isopropylpyrrolo[1,2-f]triazine-6-carboxylate (see US2004/63708A1) (40.0 mg, 0.16 mmol) and N-cyclopropyl 3-amino-4-fluorobenzamide (see WO 04/001059) (40.0 mg, 0.206) in acetonitrile (2 mL) was stirred at reflux temperature for 2 hrs. The mixture was concentrated and the residue was neutralized with $NaHCO_3$ solution. The mixture was extracted with ethyl acetate (2×5 mL). The combined extract was combined, dried and concentrated. The residue was purified by column chromatography (Ethyl acetate:hexanes/1:3) to afford a solid product, 27 mg (41% yield). $^1$H NMR ($CDCl_3$+$CD_3OD$) δ 8.79 (m, 1 H), 8.07 (s, 1 H), 8.00 (s, 1 H), 7.61 (m, 1 H), 7.24 (m, 1 H), 4.16 (m, 1 H), 3.89 (s, 3 H), 2.91 (m, 1 H), 1.55 (d, J=7.1 Hz, 6 H), 0.88 9 (m, 2 H), 0.67 (m, 2 H). MS: m/e 412 $(M+H)^+$.

EXAMPLE 2

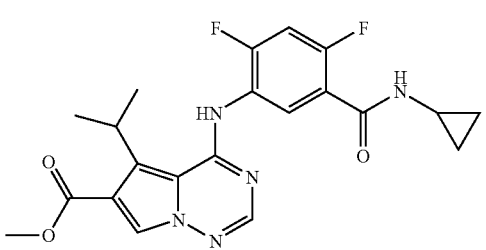

Example 2 was prepared by a procedure similar to Example 1 using N-cyclopropyl 5-amino-2,4-difluorobenzamide (89% yield). $^1$H NMR ($CDCl_3$+$CD_3OD$) δ 8.27 (m, 1 H), 7.99 (s 1 H), 7.80 (s, 1 H), 6.96 (t, J=9.9 Hz, 1 H), 3.90 (m, 1 H), 3.78 (s, 3 H), 2.80 (m, 1 H), 1.43 (d, J=7.1 Hz, 6 H), 0.76 (m, 2 H), 0.56 (m, 2 H). MS: m/e 430 $(M+H)^+$.

Step 1: The mercapto intermediate 2 in an organic solvent such as N,N-dimethylformamide from Scheme 2, is agitated with Merrifield resin to form resin bound sulfide intermediate 2.

Step 2: The formation of resin bound chloroimidate 3 is analogous to Scheme 2 with a dehydrating agent such as phosphorous oxychloride with an organic base such as diisopropylethylamine (DIPEA) in toluene at 110° C.

EXAMPLE 3

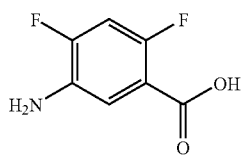

A solution of 2,4-difluoro-5-nitrobenzoic acid (purchased from Combi-Blocks Inc) (6.09 g, 30 mmol) in ethanol (80 mL) was hydrogenated with Pd/C (0.7 g, 10%) under hydrogen atmosphere for 2 hrs. The mixture was filtered and the filtrate was concentrated to afford a solid (50.10 g, 98% yield). $^1$H NMR (DMSO-d$_6$) δ 13.0 (s, 1 H), 7.29 (t, J=7.7 Hz, 1 H), 7.12 (t, J=11.0 Hz, 1 H), 5.24 (s, 2 H). MS: m/e 174 (M+H)$^+$.

EXAMPLE 4

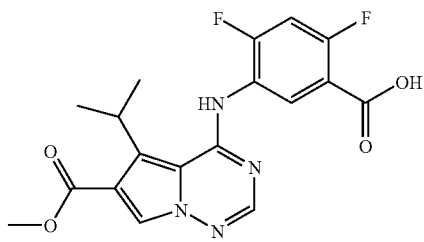

The compound of Example 4 was prepared by a procedure similar to Example 1 using the compound of Example 3 (97% yield). $^1$H NMR (DMSO-d$_6$) δ 7.91 (s, 1 H), 7.58 (s, 1 H), 7.57 (m, 1 H), 7.44 (t, J=11.0 Hz, 1 H), 4.34 (m, 1 H), 3.77 (s, 3 H), 1.37 (d, J=7.1 Hz, 6 H). MS: m/e 391 (M+H)$^+$.

EXAMPLE 5

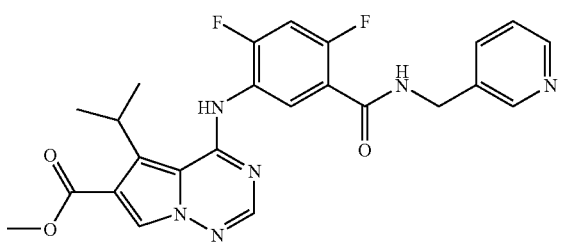

A mixture of the compound of Example 4 (19.0 mg, 0.05 mmol), 3-aminomethylpyridine (10.8 mg, 0.1 mmol) and BOP reagent (25 mg) was stirred in DMF (0.3 mL) and triethylamine (0.05 mL) at room temperature for 1 hr. Water (2 mL) was added to the mixture and the precipitate was formed. The precipitate was collected, washed with water and dried to afford the desired product, as a colorless solid (18.0 mg, 75% yield). $^1$H NMR (DMSO-d$_6$) δ 8.92 (s, 1 H), 8.56 (s, 1 H), 8.46 (s, 1 H), 7.80 (m, 1 H), 7.73 (d, J=6.2 Hz, 1 H), 7.58 (m, 1 H), 7.44 (m, 1 H), 7.36 (m, 1 H), 4.48 (d, J=5.2 Hz, 2 H), 4.4 (m, 1 H), 3.77 (s, 3 H), 1.36 (d, J=7.1 Hz, 6H). MS: m/e 481 (M+H)$^+$.

Examples 6 to 14 were prepared using a procedure similar to that described for the preparation of Example 5 using the appropriate amines. The general structure of the compounds prepared in Examples 6 to 14 is shown below, wherein the R$^5$ substituent is listed in Table I for each example.

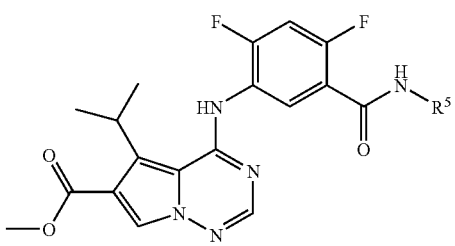

TABLE I

| Example # | R$^5$ | LC/MS; (M + H)$^+$ |
|---|---|---|
| 6 | 2-pyridylmethyl | 481 |
| 7 | 4-pyridylmethyl | 481 |
| 8 | sec-butyl | 418 |
| 9 | benzimidazol-2-ylmethyl | 520 |
| 10 | imidazol-2-ylmethyl | 470 |
| 11* | imidazol-4-ylmethyl | 470 |
| 12* | 1-methylimidazol-4-ylmethyl | 484 |
| 13 | 3-pyridyl | 467 |

TABLE I-continued

| Example # | R⁵ | LC/MS; (M + H)⁺ |
|---|---|---|
| 14 | 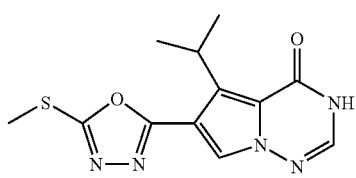 | 467 |

*The amines were prepared in a similar manner according to the literature [J. Pharm. Sci. 62 (3), 404 (1973)].

EXAMPLE 15

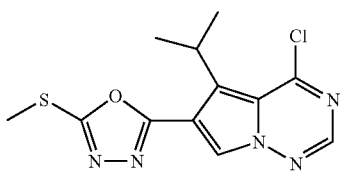

A mixture of 5-isopropyl-4-oxo-3,4-dihydropyrrolo[1,2-f]triazine-6-carbohydrazide (18.8 g, 80 mmol) and thiocarbonyldiimidazole (90% purity, 19.0 g, 96 mmol) in DMF (100 ml) was stirred at room temperature for 2 hrs, then heated at 100° C. for 1 hr. The mixture was cooled to 0° C. To this, methyl iodide (22.7 g, 160 mmol) was added. The resulting mixture was stirred at room temperature for 1 hr. To this ice water (200 ml) was added. The precipitate was collected by filtration, rinsed with water. The solid was dried in vacuo to afford Example 15 (21.13 g, 91% yield), MS: m/e 292 (M+H)⁺.

EXAMPLE 16

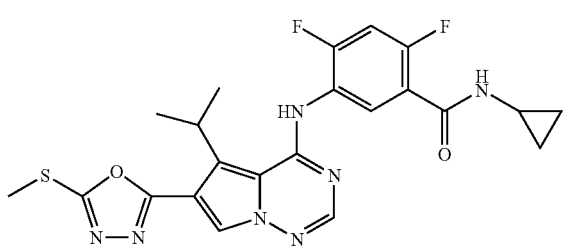

A mixture of the compound of Example 15 (5.82 g, 20 mmol) in phosphorous oxychloride (20 ml) was heated at reflux for 16 hrs. Excess phosphorous oxychloride was removed in vacuo. The residue was dissolved in dichloromethane and washed with saturated sodium bicarbonate aqueous solution. The organic layer was passed through a short pad of silica gel, eluting with 10% ethyl acetate in dichloromethane to afford a yellow solid (4.45 g, 72% yield). The compound was used for the next step without further purification.

EXAMPLE 17

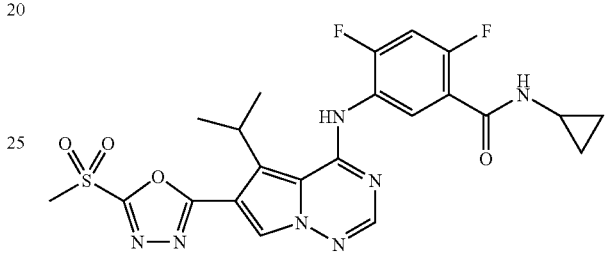

A mixture of Example 16 (2.15 g, 7.0 mmol) and N-cyclopropyl 5-amino-2,4-difluorobenzamide (1.63 g, 7.7 mmol) in acetonitrile (30 ml) was refluxed for 1 hr. The mixture was allowed to cool to room temperature, and the precipitate was collected by filtration. The solid was suspended in ethyl acetate, and washed with saturated sodium bicarbonate solution and brine. The organic layer was dried over Na₂SO₄, and concentrated to give the compound as a yellow solid (3.64 g, 75% yield). ¹H NMR (CDCl₃) δ 9.23 (m, 1 H), 8.04 (s 1 H), 7.49 (s, 1 H), 7.02 (t, J=10.45 Hz, 1 H), 6.73 (d, J=11.5 Hz, 1 H), 4.20 (m, 1H), 2.94 (m, 1 H), 2.79 (s, 3 H), 1.57 (d, J=7.2 Hz, 6 H), 0.91 (m, 2 H), 0.65 (m, 2 H). MS: m/e 486 (M+H)⁺.

EXAMPLE 18

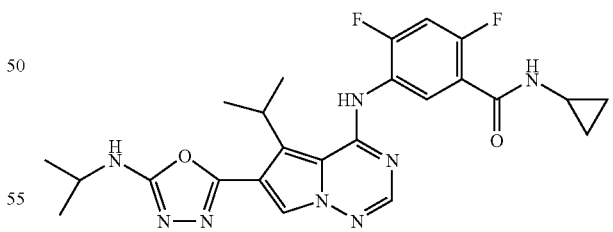

To the solution of Example 17 (1.32 g, 2.72 mmol) in 20 ml of CH₂Cl₂ at room temperature was added mCPBA (3.05 g, 13.6 mmol). The mixture was stirred at room temperature for 6 hrs. The reaction was quenched by adding 10% sodium thiosulfate solution. The organic layer was washed with sat. NaHCO₃, 5% K₂CO₃, and brine. The reaction mixture was dried, concentrated, and purified by column chromatography (1% MeOH in CH₂Cl₂) to afford the desired product as a light yellow solid (1.02 g, 73% yield). ¹H NMR (CDCl₃) δ 9.22 (t, J=8.8 Hz, 1 H), 8.03 (s 1 H), 7.98 (s, 1 H), 7.48 (s, 1H), 7.02 (t, J=10.45 Hz, 1 H), 6.75 (d, J=10.45 Hz, 1 H), 4.17 (m, 1 H), 3.54 (s, 3H), 2.96 (m, 1H), 1.60 (d, J=7.2 Hz, 6 H), 0.90 (m, 2 H), 0.65 (m, 2 H). MS: m/e 518 (M+H)⁺.

EXAMPLE 19

In a sealed tube, the compound of Example 18 (51.7 mg, 0.10 mmol) was dissolved in 2 ml of 1,4-dioxane. 0.1 ml of the isopropylamine was added, and heated at 80° C. for 2 hrs. The reaction mixture was concentrated and purified by prep-HPLC to afford the desired product (23 mg, 46% yield). ¹H NMR (DMSO-d₆) δ 8.36 (d, J=3.96 Hz, 1 H), 7.87 (s, 1 H), 7.61 (s, 1H), 7.39 (t, J=10.28 Hz, 1 H), 7.31 (b, 1 H), 4.19 (m, 1 H), 3.75 (m, 1H), 2.82 (m, 1 H), 1.37 (d, J=7.04 Hz, 6 H), 1.22 (d, J=6.52 Hz, 6 H), 0.67 (m, 2 H), 0.54 (m, 2 H). MS: m/e 497 (M+H)⁺.

Examples 20 to 39 were prepared using a procedure similar to that described for the preparation of Example 19 using the appropriate amines. The general structure of the compounds prepared in Examples 20 to 39 is shown below, wherein the —NR⁷R⁷' substituent is listed in Table II for each example.

EXAMPLE 20–39

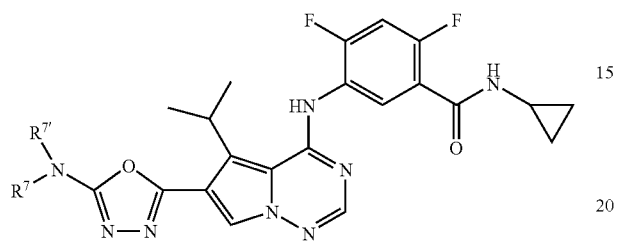

TABLE II

| Example # | —NR⁷R⁷' | LC/MS; (M + H)⁺ |
|---|---|---|
| 20 | ethanol chain | 499 |
| 21 | propyl | 497 |
| 22 | fluoroethyl | 501 |
| 23 | ethylaminoethyl | 526 |
| 24 | dimethylaminomethyl | 526 |
| 25 | (S)-2-hydroxypropyl | 513 |
| 26 | (R)-2-hydroxypropyl | 513 |
| 27 | (S)-3-hydroxypyrrolidinyl | 525 |
| 28 | neopentylamine | 540 |

TABLE II-continued

| Example # | —NR⁷R⁷' | LC/MS; (M + H)⁺ |
|---|---|---|
| 29 | piperazinyl | 524 |
| 30 | dimethylaminopropyl | 540 |
| 31 | N-Boc-4-aminopiperidinyl | 638 |
| 32 | 4-aminopiperidinyl | 538 |
| 33 | N-methyl-N-Boc-aminopropyl | 626 |
| 34 | methylaminopropyl | 526 |
| 35 | N-Boc-aminopropyl | 612 |
| 36* | aminopropyl | 512 |
| 37 | N-Boc-aminobutyl | 626 |
| 38* | aminobutyl | 526 |

*The products were prepared by the deprotection of the corresponding tert-butyloxycarbonyl (Boc) in 30–50% trifluoroacetic acid (TFA) in dichloromethane.

EXAMPLE 39

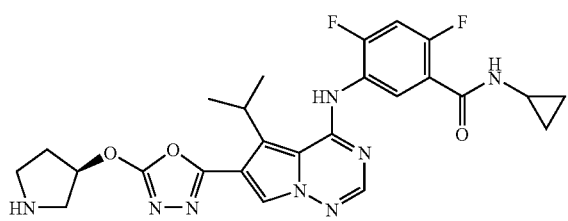

To the solution of R-(+)-3-pyrrolidinol (1.0 mmol, 87.1 mg) in a mixed solvent (2 ml of THF and 1 ml of DMF) at 0° C. was added sodium hydride (60% in mineral oil, 32 mg, 0.8 mmol). The mixture was stirred at 0° C. for 15 min, followed by the addition of Example 18 (0.1 mmol, 51.7 mg). The reaction mixture was stirred at 0° C. for 1 hr, and diluted with EtOAc. The organic solution was washed with $H_2O$ and brine, dried and concentrated. The residue was purified by prep HPLC to afford a white solid (35 mg, yield 67%). $^1$H NMR ($CDCl_3$) δ 9.23 (m, 1H), 8.04 (s, 1 H), 7.97 (s, 1H), 7.48 (b, 1H), 7.02 (t, J=10.24 Hz, 1 H), 6.76 (b, 1 H), 4.18 (m, 1 H), 3.40 (m, 1H), 3.20 (m, 2H), 2.95 (m, 2H), 2.20 (m, 2H), 1.56 (d, J=7.24 Hz, 6 H), 0.92 (m, 2 H), 0.66 (m, 2 H). MS: m/e 525 (M+H)$^+$.

Examples 40 to 47 were prepared using a procedure similar to that described for the preparation of Example 39 using the appropriate alcohols. The general structure of the compounds prepared in Examples 40 to 47 is shown below, wherein the R$^7$ substituent is listed in Table III for each example.

EXAMPLE 40–47

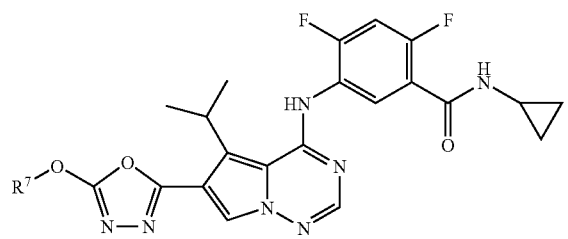

TABLE III

| Example | R$^7$ | LC/MS; (M + H)$^+$ |
|---|---|---|
| 40 | ⟨CH(CH$_3$)CH$_2$NH$_2$⟩ | 513 |
| 41 | ⟨CH(CH$_3$)CH$_2$NH$_2$⟩ | 513 |
| 42 | ⟨CH$_2$C(CH$_3$)$_2$NH$_2$⟩ | 527 |

TABLE III-continued

| Example | R$^7$ | LC/MS; (M + H)$^+$ |
|---|---|---|
| 43 | (pyrrolidine-NH) | 525 |
| 44 | (piperidine-NH) | 539 |
| 45 | (CH$_2$-piperidine-NH) | 553 |
| 46* | ⟨CH$_2$CH$_2$C(CH$_3$)$_2$NH$_2$⟩ | 541 |
| 47 | ⟨(CH$_2$)$_3$NH$_2$⟩ | 513 |

*The starting material 3-amino-3-methylbutan-1-ol was prepared according to a reference procedure: Synth. Comm. 4009, (1998).

EXAMPLE 48

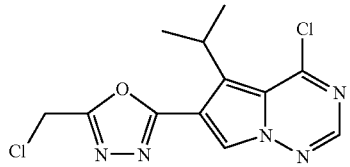

To a mixture of 5-isopropyl-4-oxo-3,4-dihydropyrrolo[1,2-f]triazine-6-carbohydrazide (2.35 g, 10 mmol) and pyridine (3 ml) in tetrahydrofuran (10 ml) and N,N-dimethylformamide (10 ml) at 0° C., was added chloroacetyl chloride (1.36 g, 12 mmol) The mixture was stirred at 0° C. for 3 hrs and at room temperature for 2 hrs. The solvents were removed in vacuo, and the residue was diluted with water and extracted with ethyl acetate. The organic layer was washed with 10% LiCl aqueous solution, dried over $Na_2SO_4$, and concentrated to give a brown oil, which was dissolved in phosphorous oxychloride (15 ml). The resulting mixture was refluxed for 3 hrs. The excess phosphorous oxychloride was removed in vacuo. The residue was dissolved in ethyl acetate and washed with sat. $NaHCO_3$ aqueous solution. The organic layer was separated, passed through a short pad of silica gel, eluting with ethyl acetate, and concentrated to give a solid which was used for next step reaction without further purification.

EXAMPLE 49

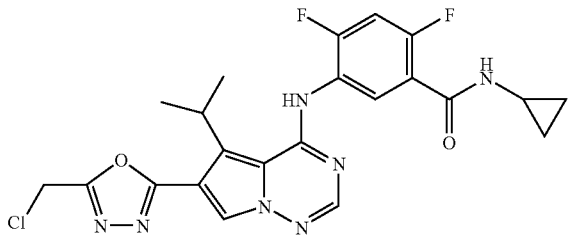

A mixture of Example 48 and N-cyclopropyl 5-amino-2,4-difluorobenzamide (1.01 g, 5 mmol) in acetonitrile (10 ml) was refluxed for 2 hrs. The solvent was removed, and the product was purified by flash column chromatography (silica gel, 3% methanol in dichloromethane) to give a yellow solid (710 mg, 29% yield). $^1$H NMR (CDCl$_3$/CD$_3$OD) δ 8.75 (s, br, 1H), 8.06 (s, 1H), 8.09 (s, 1H), 7.91(s, 1 H), 7.33 (s, 1 H), 7.05(m, 1H), 4.81 (s, 2H), 4.20 (m, 1H), 2.92 (m, 1H), 1.56 (d, J=7.15 Hz, 6 H), 0.90 (m, 2 H), 0.66 (m, 2 H). MS: m/e 488 (M)$^+$.

EXAMPLE 50

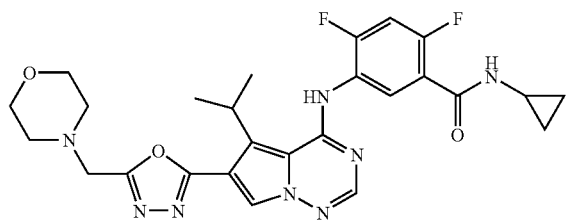

To a solution of Example 49 (40 mg, 0.082 mmol) in 1,4-dioxane (1 ml) was added 0.1 ml of morpholine (0.1 ml). The resulting mixture was stirred at room temperature for 15 hrs. The reaction mixture was concentrated and purified by prep HPLC to afford a white solid as a TFA salt (33 mg, yield 61%. $^1$H NMR (DMSO-d$_6$) δ 8.06 (s, 1 H), 8.06 (s, 1H), 7.47 (t, J=10.36 Hz, 1 H), 7.24 (b, 1 H), 4.25 (d, J=6.32 Hz, 2 H), 3.24 (m, 2H), 3.04 (m, 2H), 2.76 (m, 1H), 2.60 (m, 2H), 1.99 (m, 1H), 1.99 (m, 1H), 1.72 (m, 2H), 1.31 (d, J=6.96 Hz, 6 H), 1.24 (m, 1H), 0.61 (m, 2 H), 0.48 (m, 2 H). MS: m/e 553 (M+H)$^+$.

EXAMPLE 51

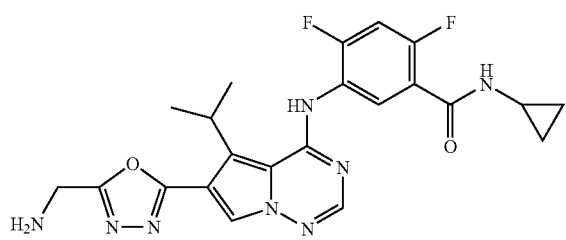

A mixture of Example 49 (40 mg, 0.082 mmol) and concentrated ammonium hydroxide (1.0 ml) in THF (1.0 ml) in a sealed tube, was heated at 90° C. for 3 hrs. After cooling to room temperature, the reaction mixture was concentrated and purified by prep HPLC to afford a white solid as a TFA salt (21 mg, yield 45%). $^1$H NMR (CD$_3$OD) δ 8.01 (s, 1 H), 7.63 (b, 1H), 7.56 (s, 1H), 7.19 (t, J=10.24 Hz, 1H), 4.55 (s, 2 H), 4.28 (m, 1H), 2.87(m, 1H), 1.51(d, J=7.16 Hz, 6 H), 0.82(m, 2 H), 0.64 (m, 2 H). MS: m/e 469 (M+H)$^+$.

EXAMPLE 52

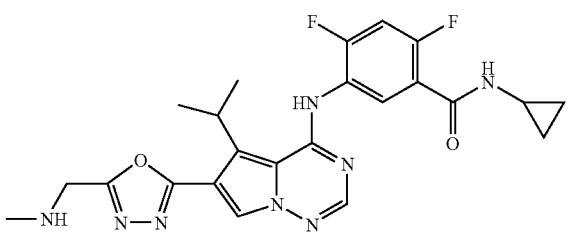

This compound was prepared in a similar procedure as Example 52 using aqueous methyl amine, 53% yield. $^1$H NMR (CD$_3$OD) δ 8.01 (s, 1 H), 7.64 (t, J=8.25 Hz, 1H), 7.56 (s, 1H), 7.18 (t, J=10.24 Hz, 1 H), 4.66 (s, 2H), 4.28 (m, 1H), 2.94 (s, 3H), 2.87(m, 1H), 1.51(d, J=7.16 Hz, 6 H), 0.82(m, 2 H), 0.64 (m, 2 H). MS: m/e 483 (M+H)$^+$.

EXAMPLE 53

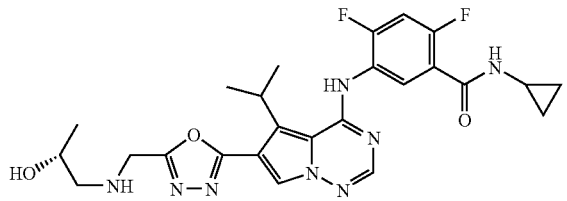

A mixture of Example 49 (40 mg, 0.082 mmol) and (R)-(−)-1-amino-2-propanol (62 mg, 0.82 mmol) in 1,4-dioxane (1.0 ml) was heated at 45° C. for 15 hrs. The reaction mixture was concentrated and purified by prep HPLC to afford the desired product, yield 61%. $^1$H NMR (CD$_3$OD) δ 8.02 (s, 1 H), 7.65 (t, J=8.25 Hz, 1H), 7.56 (s, 1H), 7.19 (t, J=10.24 Hz, 1 H), 4.69 (s, 2H), 4.28 (m, 1H), 4.13 (m, 1H), 3.33(m, 1H), 3.11(m, 1H), 2.87(m, 1H), 1.51(d, J=7.16 Hz, 6 H), 1.28(d, J=7.15 Hz, 3H), 0.82(m, 2 H), 0.64 (m, 2H). MS: m/e 527 (M+H)$^+$.

Examples 54 to 62 were prepared using a procedure similar to that described for the preparation of Example 53 using the appropriate amines. The general structure of the compounds prepared in Examples 54 to 62 is shown below, wherein the —NR$^8$R$^{8'}$ substituent is listed in Table IV for each example.

EXAMPLE 54–62

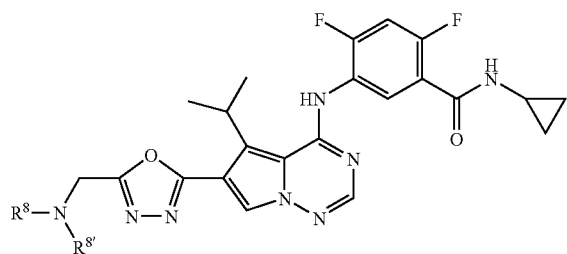

TABLE IV

| Example # | —NR⁸R⁸' | LC/MS; (M + H)⁺ |
|---|---|---|
| 54 | | 527 |
| 55 | | 539 |
| 56 | | 539 |
| 57 | | 538 |
| 58 | | 497 |
| 59 | | 511 |
| 60 | | 497 |
| 61 | | 513 |
| 62 | | 527 |

EXAMPLE 63

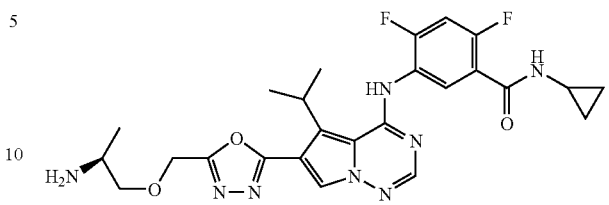

To a solution of (s)-(+)-1-amino-2-propanol (49 mg, 0.65 mmol) in 1 ml of THF at room temperature was added sodium hydride (60% in mineral oil, 26 mg, 0.65 mmol). The mixture was stirred at room temperature for 30 min, and then cooled to 0° C. To this the compound of Example 49 (31 mg, 0.065 mmol)) was added. The reaction mixture was stirred at 0° C. for 2 hrs, and quenched by adding ice water. The mixture was extracted with EtOAc. The organic extracts were dried concentrated, and purified by prep HPLC to afford a white solid as a TFA salt (13 mg, 31% yield). ¹H NMR (CD₃OD) δ 7.92 (s, 1 H), 7.56 (t, J=8.25 Hz, 1H), 7.48(s, 1H), 7.09 (t, J=10.24 Hz, 1 H), 4.80(s, 2H), 4.16 (m, 1H), 3.91 (m, 1H), 3.05(m, 1H), 2.88(m, 1H), 2.77(m, 1H), 1.41(d, J=7.16 Hz, 6 H), 1.24(d, J=6.05 Hz, 3H), 0.72(m, 2 H), 0.55(m, 2 H). MS: m/e 527 (M+H)⁺.

EXAMPLE 64

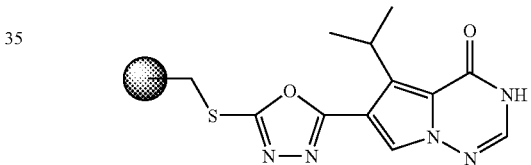

A mixture of hydrazide (2.35 g, 10 mmol) and thiocarbonyldiimidazole (2.14 g, 12 mmol) in DMF (20 ml) was stirred at room temperature overnight. The mixture was heated at 100° C. for 2 hrs. After cooling down to rt, the Merrifield resin (loading 1.53 mmol/g, 3.27 g, 5 mmol) was added. The resulting suspension was agitated for 2 days. The resin was filtered, washed with 50% DMF/H₂O (2×), MeOH (3×), and CH₂Cl₂ (3×), dried to give 4.28 g of the compound.

EXAMPLE 65

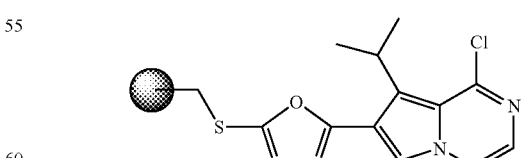

A mixture of sulfide resin (Example 64, 1 g, 1.23 mmol), DIPEA (192 mg, 1.48 mmol), and POCl₃ (283 mg, 1.845 mmol) in toluene (30 ml) was refluxed for 8 hrs. The resin was filtered, and washed with CH₂Cl₂ (6×), and dried for the next step of the reaction.

EXAMPLE 66

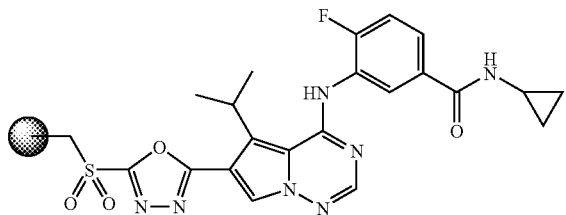

A mixture of chloride resin (Example 65, 400 mg) and 3-amino-N-cyclopropyl-4-fluorobenzamide (1.5 mmol) in acetonitrile (3 ml) and 1,2-dichloroethane (3 ml) was heated at 80° C. with gentle stirring for 10 hrs. The resin was washed with 50% DMF/H$_2$O (2×), MeOH (3×), and CH$_2$Cl$_2$ (3×), dried in vacuo. The resin was agitated with mCPBA (77% max, 400 mg and Na$_2$SO$_4$ (2 g) in CH$_2$Cl$_2$ (25 ml) for 3 hrs. CH$_2$Cl$_2$ was added and the resin was suspended on top of the mixture, and decanted to a tube with frit at bottom. The resulting sulfone resin was washed with 50% DMF/5% Na$_2$SO$_3$ aq. Solution (2×), DMF/H$_2$O (50%) (2×), MeOH (3×), and CH$_2$Cl$_2$ (3×), and dried in vacuo.

EXAMPLE 67

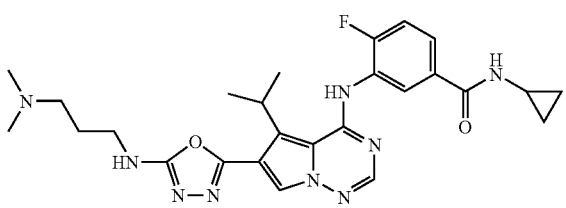

A mixture of Example 66 (80 mg) and 3-(dimethylamino)propylamine (65 mg, 0.64 mmol) in dioxane (0.8 ml) was heated at 115° C. in a sealed tube for two hrs. The resin was filtered, rinsed with methanol. The filtrate was concentrated, and purified by prep-HPLC to afford a white solid (9 mg) as a TFA salt. $^1$H NMR (DMSO) δ 9.52 (br, 1 H), 8.42 (s, 1H), 7.80(t, J=4.95 Hz, 1H), 7.60 (br, 1H), 7.33 (t, J=9.35 Hz, 1 H), 3.33(m, 2H), 3.16 (m, 2H), 2.85 (m, 1H), 2.80(d, J=4.40 Hz, 6H), 1.98(m, 2H), 1.41(d, J=7.15 Hz, 6 H), 0.70(m, 2 H), 0.55(m, 2 H). MS: m/e 522 (M+H)$^+$.

Examples 68 to 75 were prepared using a procedure similar to that described for the preparation of Example 67 using the appropriate amines. The general structure of the compounds prepared in Examples 68 to 75 is shown below, wherein the —NR$^9$R$^{10}$ substituent is listed in Table V for each example.

EXAMPLE 68–75

[General structure: same core as Example 67 with R$^9$R$^{10}$N– substituent on the oxadiazole]

TABLE V

| Example # | —NR$^9$R$^{10}$ | LC/MS; (M + H)$^+$ |
|---|---|---|
| 68 | —NH(CH$_2$)$_3$NHC(O)O-t-Bu | 594 |
| 69* | —NH(CH$_2$)$_3$NH$_2$ | 494 |
| 70 | (3-Boc-amino)pyrrolidin-1-yl | 606 |
| 71* | (3-amino)pyrrolidin-1-yl | 506 |
| 72 | (3-Boc-amino)pyrrolidin-1-yl (enantiomer) | 606 |
| 73* | (3-amino)pyrrolidin-1-yl (enantiomer) | 506 |
| 74 | (1-Boc-pyrrolidin-3-yl)amino | 606 |

TABLE V-continued

| Example # | —NR⁹R¹⁰ | LC/MS; (M + H)⁺ |
|---|---|---|
| 75* | 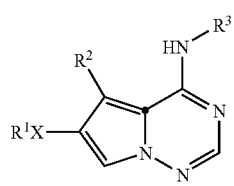 | 506 |

*The products were prepared by the deprotection of the corresponding tert-butyloxycarbonyl (Boc) in 30–50% trifluoroacetic acid (TFA) in dichloromethane.

What is claimed is:

1. A compound of formula (I):

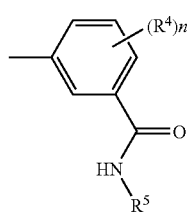
(I)

or an enantiomer, diastereomer, or pharmaceutically acceptable salt, thereof, wherein X is —O—,

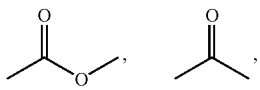

—OCONH—, —S—, —SO— or —SO$_2$—, or X is absent;

$R^1$ is hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl or substituted heterocycloalkyl;

$R^2$ is isopropyl;

$R^3$ is

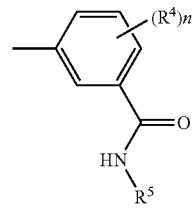

wherein each $R^4$ is independently selected from hydrogen, halogen or alkyl;

n is 0, 1 or 2; and $R^5$ is hydrogen, alkyl, substituted alkyl, cycloalkyl, substituted cycloalkyl, heterocyclyl or substituted heterocyclyl.

2. The compound according to claim 1 wherein

X is —O—,

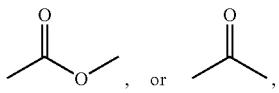

or X is absent;

$R^1$ is alkyl, substituted alkyl, aryl, substituted aryl, heterocyclo, substituted heterocyclo, aralkyl, substituted aralkyl, heterocycloalkyl or substituted heterocycloalkyl;

$R^2$ is isopropyl;

$R^3$ is

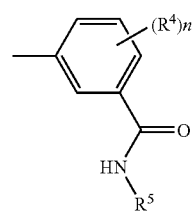

wherein each $R^4$ is independently selected from hydrogen or halogen;

n is 1 or 2; and $R^5$ is cycloalkyl.

3. The compound according to claim 2 wherein

X is absent;

$R^1$ is heterocyclo, substituted heterocyclo, heterocycloalkyl or substituted heterocycloalkyl;

$R^2$ is isopropyl;

$R^3$ is

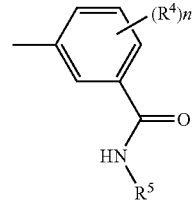

wherein each $R^4$ is independently selected from hydrogen or fluorine;

n is 1 or 2; and $R^5$ is cyclopropyl.

4. The compound according to claim 3 wherein

X is absent;

$R^1$ is oxadizole or substituted oxadiazole;

$R^2$ is isopropyl;

$R^3$ is wherein each $R^4$ is independently selected from hydrogen or fluorine;

n is 1 or 2; and $R^5$ is cyclopropyl.

5. The compound selected from the group consisting of:
methyl 4-(5-(cyclopropylcarbamoyl)-2-fluorophenylamino)-5-isopropylpyrrolo[1,2-f][1,2,4]triazine-6-carboxylate,
methyl 4-(5-(cyclopropylcarbamoyl)-2,4-difluorophenylamino)-5-isopropylpyrrolo[1,2-f][1,2,4]triazine-6-carboxylate,
N-cyclopropyl-2,4-difluoro-5-(5-isopropyl-6-(5-(isopropylamino)-1,3,4-oxadiazol-2-yl)pyrrolo[1,2-f][1,2,4]triazin-4-ylamino)benzamide,
N-cyclopropyl-2,4-difluoro-5-(6-(5-(2-hydroxyethylamino)-1,3,4-oxadiazol-2-yl)-5-isopropylpyrrolo[1,2-f][1,2,4]triazin-4-ylamino)benzamide,
N-cyclopropyl-2,4-difluoro-5-(5-isopropyl-6-(5-(propylamino)-1,3,4-oxadiazol-2-yl)pyrrolo[1,2-f][1,2,4]triazin-4-ylamino)benzamide,
N-cyclopropyl-2,4-difluoro-5-(6-(5-(2-fluoroethylamino)-1,3,4-oxadiazol-2-yl)-5-isopropylpyrrolo[1,2-f][1,2,4]triazin-4-ylamino)benzamide,
N-cyclopropyl-5-(6-(5-(2-(ethylamino)ethylamino)-1,3,4-oxadiazol-2-yl)-5-isopropylpyrrolo[1,2-f][1,2,4]triazin-4-ylamino)-2,4-difluorobenzamide,
5-(6-(5-(2-amino-2-methylpropylamino)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-2,4-difluoro-5-(6-(5-((S)-2-hydroxypropylamino)-1,3,4-oxadiazol-2-yl)-5-isopropylpyrrolo[1,2-f][1,2,4]triazin-4-ylamino)benzamide,
N-cyclopropyl-2,4-difluoro-5-(6-(5-((R)-2-hydroxypropylamino)-1,3,4-oxadiazol-2-yl)-5-isopropylpyrrolo[1,2-f][1,2,4]triazin-4-ylamino)benzamide,
N-cyclopropyl-2,4-difluoro-5-(6-(5-((R)-3-hydroxypyrrolidin-1-yl)-1,3,4-oxadiazol-2-yl)-5-isopropylpyrrolo[1,2-f][1,2,4]triazin-4-ylamino)benzamide,
5-(6-(5-(3-amino-2,2-dimethylpropylamino)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-2,4-difluoro-5-(5-isopropyl-6-(5-(piperazin-1-yl)-1,3,4-oxadiazol-2-yl)pyrrolo[1,2-f][1,2,4]triazin-4-ylamino)benzamide,
N-cyclopropyl-5-(6-(5-(3-(dimethylamino)propylamino)-1,3,4-oxadiazol-2-yl)-5-isopropylpyrrolo[1,2-f][1,2,4]triazin-4-ylamino)-2,4-difluorobenzamide,
5-(6-(5-(4-aminopiperidin-1-yl)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-2,4-difluoro-5-(5-isopropyl-6-(5-(3-(methylamino)propylamino)-1,3,4-oxadiazol-2-yl)pyrrolo[1,2-f][1,2,4]triazin-4-ylamino)benzamide,
5-(6-(5-(3-aminopropylamino)-1,3,4-oxadiazol-2-yl)-5-isopropylpyrrolo[1,2-f][1,2,4]triazin-4-ylamino)-N-cyclopropyl-2,4-difluorobenzamide,
5-(6-(5-(4-aminobutylamino)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-2,4-difluoro-5-(5-isopropyl-6-(5-((R)-pyrrolidin-3-yloxy)-1,3,4-oxadiazol-2-yl)pyrrolo[1,2-f][1,2,4]triazin-4-ylamino)benzamide,
5-(6-(5-((R)-2-aminopropoxy)-1,3,4-oxadiazol-2-yl)-5-isopropylpyrrolo[1,2-f][1,2,4]triazin-4-ylamino)-N-cyclopropyl-2,4-difluorobenzamide,
5-(6-(5-((S)-2-aminopropoxy)-1,3,4-oxadiazol-2-yl)-5-isopropylpyrrolo[1,2-f][1,2,4]triazin-4-ylamino)-N-cyclopropyl-2,4-difluorobenzamide,
5-(6-(5-(2-amino-2-methylpropoxy)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-2,4-difluoro-5-(5-isopropyl-6-(5-((S)-pyrrolidin-3-yloxy)-1,3,4-oxadiazol-2-yl)pyrrolo[1,2-f][1,2,4]triazin-4-ylamino)benzamide,
N-cyclopropyl-2,4-difluoro-5-(5-isopropyl-6-(5-(piperidin-4-yloxy)-1,3,4-oxadiazol-2-yl)pyrrolo[1,2-f][1,2,4]triazin-4-ylamino)benzamide,
N-cyclopropyl-2,4-difluoro-5-(5-isopropyl-6-(5-(piperidin-4-ylmethoxy)-1,3,4-oxadiazol-2-yl)pyrrolo[1,2-f][1,2,4]triazin-4-ylamino)benzamide,
5-(6-(5-(3-amino-3-methylbutoxy)-1,3,4-oxadiazol-2-yl)-5-isopropylpyrrolo[1,2-f][1,2,4]triazin-4-ylamino)-N-cyclopropyl-2,4-difluorobenzamide,
5-(6-(5-(3-aminopropoxy)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-2,4-difluoro-5-(5-isopropyl-6-(5-(morpholinomethyl)-1,3,4-oxadiazol-2-yl)pyrrolo[1,2-f][1,2,4]triazin-4-ylamino)benzamide,
5-(6-(5-(aminomethyl)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-2,4-difluoro-5-(5-isopropyl-6-(5-((methylamino)methyl)-1,3,4-oxadiazol-2-yl)pyrrolo[1,2-f][1,2,4]triazin-4-ylamino)benzamide,
N-cyclopropyl-2,4-difluoro-5-(6-(5-(((R)-2-hydroxypropylamino)methyl)-1,3,4-oxadiazol-2-yl)-5-isopropylpyrrolo[1,2-f][1,2,4]triazin-4-ylamino)benzamide,
N-cyclopropyl-2,4-difluoro-5-(6-(5-(((S)-2-hydroxypropylamino)methyl)-1,3,4-oxadiazol-2-yl)-5-isopropylpyrrolo[1,2-f][1,2,4]triazin-4-ylamino)benzamide,
N-cyclopropyl-2,4-difluoro-5-(6-(5-(((R)-3-hydroxypyrrolidin-1-yl)methyl)-1,3,4-oxadiazol-2-yl)-5-isopropylpyrrolo[1,2-f][1,2,4]triazin-4-ylamino)benzamide,
N-cyclopropyl-2,4-difluoro-5-(6-(5-(((S)-3-hydroxypyrrolidin-1-yl)methyl)-1,3,4-oxadiazol-2-yl)-5-isopropylpyrrolo[1,2-f][1,2,4]triazin-4-ylamino)benzamide,
N-cyclopropyl-2,4-difluoro-5-(5-isopropyl-6-(5-(piperazin-1-ylmethyl)-1,3,4-oxadiazol-2-yl)pyrrolo[1,2-f][1,2,4]triazin-4-ylamino)benzamide,
N-cyclopropyl-5-(6-(5-((dimethylamino)methyl)-1,3,4-oxadiazol-2-yl)-5-isopropylpyrrolo[1,2-f][1,2,4]triazin-4-ylamino)-2,4-difluorobenzamide,
N-cyclopropyl-2,4-difluoro-5-(5-isopropyl-6-(5-((isopropylamino)methyl)-1,3,4-oxadiazol-2-yl)pyrrolo[1,2-f][1,2,4]triazin-4-ylamino)benzamide,
N-cyclopropyl-5-(6-(5-((ethylamino)methyl)-1,3,4-oxadiazol-2-yl)-5-isopropylpyrrolo[1,2-f][1,2,4]triazin-4-ylamino)-2,4-difluorobenzamide,
N-cyclopropyl-2,4-difluoro-5-(6-(5-((2-hydroxyethylamino)methyl)-1,3,4-oxadiazol-2-yl)-5-isopropylpyrrolo[1,2-f][1,2,4]triazin-4-ylamino)benzamide,
N-cyclopropyl-2,4-difluoro-5-(6-(5-((2-methoxyethylamino)methyl)-1,3,4-oxadiazol-2-yl)-5-isopropylpyrrolo[1,2-f][1,2,4]triazin-4-ylamino)benzamide,
5-(6-(5-(((S)-2-aminopropoxy)methyl)-1,3,4-oxadiazol-2-yl)-5-isopropylpyrrolo[1,2-f][1,2,4]triazin-4-ylamino)-N-cyclopropyl-2,4-difluorobenzamide,
N-cyclopropyl-3-(6-(5-(3-(dimethylamino)propylamino)-1,3,4-oxadiazol-2-yl)-5-isopropylpyrrolo[1,2-f][1,2,4]triazin-4-ylamino)-4-fluorobenzamide, 3-(6-(5-(3-aminopropylamino)-1,3,4-oxadiazol-2-yl)-5-isopropylpyrrolo[1,2-f][1,2,4]triazin-4-ylamino)-N-cyclopropyl-4-fluorobenzamide, 3-(6-(5-((S)-3-aminopyrrolidin-1-yl)-1,3,4-oxadiazol-2-yl)-5-isopropylpyrrolo[1,2-f][1,2,4]triazin-4-ylamino)-N-cyclopropyl-4-fluorobenzamide, 3-(6-(5-((R)-3-aminopyrrolidin-1-yl)-1,3,4-oxadiazol-2-yl)-5-isopropylpyrrolo[1,2-f][1,2,4]triazin-4-ylamino)-N-cyclopropyl-4-fluorobenzamide, N-cyclopropyl-4-fluoro-3-(5-isopropyl-6-(5-(pyrrolidin-3-ylamino)-1,3,4-oxadiazol-2-yl)pyrrolo[1,2-f][1,2,4]triazin-4-ylamino)benzamide, or a pharmaceutically acceptable salt, thereof.

6. A pharmaceutical composition comprising one or more of the compounds of claim 1 and a pharmaceutically acceptable carrier.

* * * * *